US006479075B1

(12) United States Patent
Odidi et al.

(10) Patent No.: US 6,479,075 B1
(45) Date of Patent: Nov. 12, 2002

(54) PHARMACEUTICAL FORMULATIONS FOR ACID LABILE SUBSTANCES

(76) Inventors: Isa Odidi, 2136 Opal Court, Mississauga, Ontario, L5K 2S5 (CA); Amina Odidi, 2136 Opal Court, Mississauga, Ontario, L5K 2S5 (CA)

(*) Notice: Subject to any disclaimer, the term of this patent is extended or adjusted under 35 U.S.C. 154(b) by 0 days.

(21) Appl. No.: 09/767,028

(22) Filed: Jan. 22, 2001

Related U.S. Application Data

(63) Continuation of application No. 09/166,274, filed on Oct. 5, 1998, now Pat. No. 6,296,876.
(60) Provisional application No. 60/061,211, filed on Oct. 6, 1997, and provisional application No. 60/068,517, filed on Dec. 22, 1997.

(51) Int. Cl.[7] .............................. A61K 9/14; A61K 9/32; A61K 9/34; A61K 9/36; A61K 9/54
(52) U.S. Cl. ..................... 424/458; 424/456; 424/461; 424/462; 424/479; 424/480; 424/481; 424/482; 424/494; 424/495; 424/496; 424/497; 514/770; 514/772.3; 514/777; 514/778; 514/782; 514/970
(58) Field of Search ................. 424/458, 461, 424/462, 475, 480, 482, 494, 495, 497, 496, 481, 456, 479

(56) References Cited

U.S. PATENT DOCUMENTS

| 2,540,979 | A | | 2/1951 | Clymer et al. ............... 167/82 |
|---|---|---|---|---|
| 4,786,505 | A | | 11/1988 | Lovgren et al. ............. 424/468 |
| 4,853,230 | A | | 8/1989 | Lovgren et al. ............. 424/466 |
| 5,879,708 | A | * | 3/1999 | Makino et al. ............. 424/475 |

FOREIGN PATENT DOCUMENTS

| DE | 1 204 363 | 4/1965 |
|---|---|---|
| EP | 0 005129 B1 | 4/1981 |
| EP | A0342522 | 11/1989 |
| WO | 85/03436 | 8/1985 |

OTHER PUBLICATIONS

Rakur et al; "2–((2–Pyridylmethyl) Sulfinyl) Benzimidazoles: Acid Sensitive Suicide Inhibitors of the Proton Transport System in the Parietal Cell", Biochem. Biophys. Res. Comm., 128(1):477, (1985).

* cited by examiner

Primary Examiner—James M. Spear
(74) Attorney, Agent, or Firm—Isabelle M. Clauss; Foley Hoag LLP

(57) ABSTRACT

This invention in general relates to novel pharmaceutical compositions for acid labile substances as well as for methods of making such. Specifically, the invention provides a pharmaceutical composition comprising about 1 to 75% by weight acid labile compound, up to about 5% by weight disintegrant, at least one protector coat layer used to separate and protect the acid labile substance from acid reacting groups and gastric juice, and at least one enteric coat layer which surrounds the protector coating layer and ensures delivery of over 80% the acid labile substance to the small intestine.

15 Claims, No Drawings

PHARMACEUTICAL FORMULATIONS FOR ACID LABILE SUBSTANCES

This application is a continuation of U.S. Pat. application Ser. No. 09/166,274, now U.S. Pat. No. 6,296,876 filed Oct. 5,1998, which claims the benefit of U.S. Provisional Application Serial No. 60/061,211 filed Oct. 6, 1997 and U.S. Provisional Application Serial No. 06/068,517 filed Dec. 22, 1997.

FIELD OF THE INVENTION

This invention in general relates to novel pharmaceutical compositions for acid labile substances as well as for methods of making such.

BACKGROUND OF THE INVENTION

Substituted benzimidazoles are substituted sulfoxides which are potent inhibitors of gastric acid secretion. Such substituted sulfoxides are described for example in EP 0005129. These compounds are susceptible to degradation and/or transformation in both acid and neutral media. The acidic decomposition of these acid labile compounds is due to an acid catalyzed reaction described by G. Rackur et al., in Biochem. Biophys. Res. Commun. 1985: 128(1). P477–484.

In order to provide a pharmaceutical composition containing such acid labile substances which is not degraded in the gastrointestinal tract, the acid labile substances must be enteric coated. However, pharmaceutically acceptable enteric coating materials are acidic in nature or contain acid reacting groups. Therefore, if the acid labile substances are directly covered by these enteric coating materials, the acid labile substance rapidly degrades.

U.S. Pat. Nos. 4,853,230 and 4,786,505 describe enteric coated pharmaceutical formulations of acid labile substances for oral use, where the cores contain acid labile drugs mixed with alkaline reacting substances. This is then coated with a first separating layer which is rapidly disintegrated in gastric fluid and a final enteric layer. However, the alkaline reacting substances in the core do not completely protect the acid labile substances from degradation and thus additional pH buffering substances are required. These formulations may also contain aluminum, potassium, sodium, calcium and magnesium which compounds or composites may be of concern for oral ingestion in humans.

U.S. Pat. No. 2,540,797 describes an enteric coated pharmaceutical in an oral dosage form, where the enteric coating is combined with a second and/or first coating of water insoluble "wax" layer. This coating is not suitable as direct contact with acid labile substances as it will result in degradation of the acid labile active.

WO No. 85/03436 discloses a pharmaceutical preparation in which the core contains active drugs mixed with buffering compounds such as sodium dihydrogenphosphate which maintains a constant pH. A coating material is used to provide a constant rate of diffusion of the pharmaceutical active. However, this formulation is not suitable for acid labile compounds where a rapid release in the small intestine is required. The direct application of an enteric coating onto the pharmaceutical active would adversely influence the storage stability of the acid labile compounds contained therein.

DE-A1-1 204 363 describes a three layer coating method for pharmaceuticals. The first coating layer is a surface membrane soluble in gastric but insoluble in intestinal juice. The second coating layer is soluble at all physiological pHs and the third coating layer is an enteric coating. This method is complicated and is also not suitable for acid labile compounds such as substituted benzimidazoles where rapid release of the drug in the small intestine is required, as it results in a dosage form which is not dissolved in gastric juice and dissolves slowly in the small intestine.

There was therefore a need to develop a pharmaceutical composition for acid labile substances that adequately protected the acid labile active prior to its being released in the small intestine. Accordingly, a novel pharmaceutical composition was developed for the delivery of acid labile substances to the gut which differs form known compositions and delivery mechanisms in the type of stabilizer(s) utilized, the mechanism(s) of stabilization used in the core containing the acid labile compound(s), by the type of protector coat applied to the core(s), the mechanism(s) by which the protector coat elicits it's protective action and the type of enteric coating compound(s) used in the composition. These lead to a different mechanism by which the acid labile drug is released in the small intestine to provide a stabilized acid labile compound composition.

SUMMARY OF THE INVENTION

The present invention provides an enteric coated dosage form of a selected acid labile compound, in particular proton pump inhibitor compounds which decrease production of acid in the gut. Such compounds include but are not limited to a omeprazole, 5-methoxy-2-(4-methoxy-3, 5 dimethyl-2-pyridinyl methyl sulfinyl-1H-benzimidazole, lansoprazole, 2-(2-diriiethylaminobenzyl)sulfinyl-benzimidazole and their related compounds such as their salts which rapidly disintegrate in the small intestine.

The novel pharmaceutical composition comprises an acid labile compound or an alkaline salt of the labile compound. The composition optionally comprises acid sequestering compound(s), and further comprises disintegrants and at least one coating layer which is swellable and/or permeable at physiological pH (preferably >5.0). This first coating layer separates and protects the core containing the acid labile active from the outer enteric coating layers.

According to an object of the present invention there is provided a pharmaceutical composition comprising:
— about 1 to 75% by weight acid labile compound;
— up to about 5% by weight disintegrant;
— at least one protector coat layer used to separate and protect the acid labile substance from acid reacting groups and gastric juice; and
— at least one enteric coat layer which surrounds the protector coating layer and ensures delivery of over 80% the acid labile substance to the small intestine.

Optionally, the composition may additionally comprise not less than about 0.1% acid sequestering compound.

According to another object of the present invention is a method for preparing the novel pharmaceutical composition of the present invention.

The novel formulation of the present invention demonstrates excellent resistance to dissolution in acid media and dissolves rapidly in neutral to alkaline media. The novel acid labile substance formulation has a good stability during long term storage.

The novel pharmaceutical composition is well suited for oral administration in a dosage unit form.

DETAILED DESCRIPTION OF THE PREFERRED EMBODIMENTS

The present invention provides an enteric coated dosage form of a selected active acid labile compound, in particular proton pump inhibitor compounds which decrease production of acid in the gut. Such compounds include but are not limited to omeprazole, 5-methoxy-2-(4-methoxy-3,5 dimethyl-2-pyridinyl methyl sulfinyl-1H-benzimidazole, lansoprazole, 2-(2-diriiethylaminobenzyl)sulfinyl-benzimidazole and their related compounds such as their ammonium, sodium, magnesium and calcium salts which rapidly disintegrate in the small intestine. The active acid labile compound is present in the composition in an amount of about 1 to 75% by weight of the composition.

In order to enhance storage stability of the core containing the active acid labile substance, the composition may additionally comprise acid sequestering substances that protect the acid labile substance. Suitable acid sequestering substances for use in the composition of the present invention include but are not limited to aminoalkyl methacrylate copolymers and ethylcellulose. Most preferably is Eugragit E, a cationic copolymer based on dimethylaminoethyl methacrylate and neutral methacrylates. The acid sequestering compounds may also be mixed with inert pharmaceutical filler(s) such as lactose, starch and microcrystalline cellulose.

Disintegrants or stabilizers are used to help stabilize the active acid labile compound within the core of the composition. Suitable disintegrants for use in the composition of the present invention include sodium starch glycolate, crospovidone, pregelatinized starch, methacrylic acid DVP and croscarmellose sodium. Such disintegrants are present in an amount of not more than about 5% by weight of the composition. Preferably, 2 to 5% by weight disintegrants are incorporated into the composition. The disintegrants may be optionally mixed with inert pharmeceutical fillers such as lactose, calcium sulfate and microcrystalline, cellulose.

The active acid labile substance, optional acid sequestering substances, and disintegrants form the core of the composition. The core is then coated with a protector coat of an acid sequestering substance and/or ethylcellulose optionally containing one or more pharmaceutical excipients such as kaolin, bentonite and talc and further enteric coated with an enteric coating polymer such as, for example, shellac or hydroxypropyl methylcellulose acetate succinate which allows the dissolution of the coating in the proximal section of the small intestine. It may also allow the diffusion of gastric juice through the enteric coating into the core during transit through the stomach. The acid sequestering substance in the protector coat and/or core will react with the diffused juice to form salts. As more alkaline solution get through the protector coat during residence in the small intestine the core will disintegrate rapidly due to swelling and capillary wicking action of the disintegrant such as methacrylic acid DVP, pregelatinized starch, cross linked carboxymethyl cellulose, cross linked starch, or cross linked polyvinyl pyrollidone present in the core.

As mentioned, in order to separate and protect the core containing at least one acid labile compound from acid reacting groups such as free carboxyl groups found in enteric coating polymers which cause degradation, it must be coated with one or more layers of an acid sequestering compound such as the aminoalkyl methacrylate copolymers, preferably Eugragit E and/or ethylcellulose, optionally containing one or more pharmaceutical excipients. This "protector coat" also acts as a barrier to acid reacting groups from reaching the core containing acid labile compound(s). The protector coat is applied as one or more layers optionally containing one or more pharmaceutical excipients such as plasticizers, pigments and anti-tacking agents. The protector coat is applied using either aqueous or solvent based pan, rotor processor and/or fluidized bed coating techniques. The thickness of the protector layer(s) is not less than 0.001 mg/cm$^2$ and the amount of acid sequestering compound and or ethylcellulose is not less than 0.1% but preferably 0.5–10% respectively. One example of a preferred protector coat is that of a water soluble resin from the group of nonionic polyethylene oxide polymers having a molecular weight of over 20,000 daltons. Such polymers may comprise polyethylene oxides of molecular weight preferably between 100,000 to 15,000,000 and specifically include WSR N-10, WSR N-80L, WSR N-750, WSR N-3000, WSR-205, WSR-1105, WSR N-12K, WSR N-60K, WSR-301, WSR COAGULANT and WSR-300 (Union Carbide).

The final composition can be made into pellets or pressed into tablets using conventional pharmaceutical processes. The pellets or tables can be used as cores or placed in gelatin capsules and used as cores.

To protect the acid labile compound from the gastric juice it is preferred to use enteric coating polymers such as shellac, and/or any it's constituent aliphatic polyhydroxy acids presented as lactones, lactides and inter-esters or their derivatives. Another example of a preferred enteric coating polymer is the acetic and mono succinic acid ester of hydroxypropyl methylcellulose preferably hydroxypropyl methylcellulose acetate sucoinate, having free succinic acid not more than 10% preferably not more than 1% and weight-average molecular weight 4.5 to $12 \times 10^{-4}$ daltons measured by gel permeation chromatography. Other suitable members of the enteric cellulose esters are cellulose acetate phthalate, cellulose acetate trimellitate and hydroxypropyl methylcellulose phthalate. Enteric coating of the type methacrylic acid copolymers can also be used. Further examples of suitable enteric coating polymers are those based on methacrylic acid and methacrylic acid esters consisting of methacrylic acid polymer type A or type B or type C, or any combination thereof. These enteric coating polymer optionally contain one or more pharmaceutical excipients such as plasticizer(s), pigment(s) and colorants. Both protector and enteric coats can be applied from either aqueous, organic or mixed solvent systems. The amount of enteric coat present is not less than 0.1% and preferably 1 to 50%, most preferably 1 to 25% by weight. The enteric coat ensures delivery of over 80% the acid labile substance to the small intestine.

Finally, the process for the compounding of the compositions enumerated above forms another aspect of the embodiment of this invention. The acid sequestering compound is used to granulate the chosen pharmaceutical fillers using a fluidized bed technique, high shear granulator, blender or planetary mixer. The granulating liquid can be either aqueous, organic or mixed solvent systems and preferably containing the acid sequestering compound(s). The granules are dried in a fluid bed or tray dryer to a loss on drying (LOD) index of not more than 5%, after which they are blended with the acid labile compound(s), other excipients and disintegrant(s) in that order. The disintegrant can be incorporated intragranular and/or extragranular although the extragranular route is preferred.

The granules are formed into pellets or tablets using conventional pharmaceutical techniques. After forming they are first coated with the protector coat(s) and then with the enteric coat as previously described.

The finished product is presented as tables or pellets or both in a hard gelatin capsule. It is preferable that the tablets or hard gelatin capsules are stored together with a desiccant in order to maintain a low moisture content during long term storage. The final composition of the present invention provides that not more than 10% of the acid labile substance is released in acid media in about 2 hours and more than about 80% of the acid labile substance is released in 24 hours in alkaline media using USP dissolution apparatus I, II, III and IV.

EXAMPLES

The examples are described for the purposes of illustration and are not intended to limit the scope of the invention.

Methods of synthetic chemistry, pharmacy and pharmacology referred to but not explicitly described in this disclosure and examples are reported in the scientific literature are well known to those skilled in the art.

EXAMPLE 1

I. Composition of Tablets

| Omeprazole | 20 mg |
|---|---|
| Eudragit E | 20 mg |
| Lactose | 80 mg |
| Calcium sulfate dihydrate | 20 mg |
| Carboxymethylcellulose sodium | 20 mg |
| Microcrystalline cellulose | 20 mg |
| Sodium lauryl sulfate | 20 mg |
| PVP XL 10 | 2 mg |
| Talc | 10 mg |

Lactose, microcrystalline cellulose, sodium lauryl sulfate, carboxymethylcellulose sodium, and calcium sulfate dehydrate were blended in a planetary mixer. The blend was granulated with alcoholic solution of Eudragit E and dried in a tray dryer to an LOD of 1%. The dried granules are blended with omeprazole, talc and PVP XL 10 and pressed into tablets.

II. Composition of Protector Coated Tablets

| Tablets from 1 | 3.00 kg |
|---|---|
| Eudragit E | 0.300 kg |
| Kaolin | 0.100 kg |
| Talc | 0.050 kg |
| Acetone | 0.234 kg |
| Isopropyl alcohol | 0.281 kg |
| Ehtylcellulose 1% soln | 0.300 kg |

Finely disperse kaolin and Talc in the Eudragit E solvent mixture using a propeller mixer. Apply the protector coat solution unto the tablets in a perforated coating pan. Apply a 1–3% solution of ethylcellulose to the protector coated tablets in a perforated coating pan.

III. Composition of Enteric Coated Tablets

| Protector coated tablets from II | 3.450 kg |
|---|---|
| Shellao* | 0.052 kg |
| Talc | 0.004 kg |

Apply the enteric coating solution unto the protector coated tablets in a perforated coating pan and dry in a tray dryer if necessary. One or more of the enteric coated tablets are filled into hard gelatin capsules.

Temperature and relative humidity of the manufacturing area should be no greater than 35° C. and 50%.

EXAMPLE 2

I. Composition of Tablets

| Omeprazole | 20 mg |
|---|---|
| Eudragit E | 20 mg |
| Lactose | 90 mg |
| Calcium sulfate dihydrate | 20 mg |
| Sodium lauryl sulfate | 20 mg |
| Microcrystalline cellulose | 20 mg |
| Sodium starch glycolate | 5 mg |
| Talc | 15 mg |

Lactose, microcrystalline cellulose, calcium sulfate and sodium lauryl sulphate were blended in a planetary mixer. The blend was granulated with alcoholic solution of Eudragit E and dried in a tray dryer to an LOD of 1%. The dried granules are blended with omeprazole, talc sodium starch glycolate and pressed into tablets.

II. Composition of Protector Coated Tablet

| Tablets from I | 3.0 kg |
|---|---|
| Eudragit E | 0.3 kg |
| Kaolin | 0.10 kg |
| Talc | 0.05 kg |
| Acetone | 0.234 kg |
| Isopropyl alcohol | 0.281 kg |

Finely disperse kaolin and Talc in the Eudragit E solved mixture using a propeller mixer. Apply the protector coat solution unto the tablets in a perforated coating pan.

III. Composition of Enteric Coated Tablets

| Protector coated tablets from II | 3.450 kg |
|---|---|
| Hydroxypropyl methylcellulose acetate succinate** | 0.345 kg |

**from the following coating solution shown below for 3 kg batch

Polymer Solution

| Hydroxypropyl methylcellulose acetate succinate | 0.345 kg |
|---|---|
| Triethyl citrate | 0.041 kg |
| Ethanol/water (80:20) | 0.807 kg |
| Pigment suspension | 0.034 kg |
| Opadry | |
| Talc | 0.034 kg |
| PEG 6000 | 0.015 kg |
| Water | 0.053 kg |

Add the homogenized pigment and talc suspension to the polymer solution to form the enteric coating solution. Apply the enteric coating solution unto the protector coated tablets in perforated coating pan and dry in a tray dryer if necessary. One or more of the enteric coated tablets are filled into hard gelatin capsules.

Temperature and relative humidity of the manufacturing area should be no greater than 35° C. and 50%.

EXAMPLE 3

I. Composition of Tablets

| | |
|---|---|
| Omeprazole | 20 mg |
| Lactose | 115 mg |
| Sodium lauryl sulfate | 25 mg |
| Microcrystalline cellulose | 20 mg |
| Sodium starch glycolate | 5 mg |
| Talc | 15 mg |

Lactose, microcrystalline cellulose and sodium lauryl sulphate were blended in a planetary mixer. The blend was granulated with alcoholic solution and dried in a tray dryer to an LOD of 1%. The dried granules are blended with omeprazole, talc and sodium starch glycolate and pressed into tablets.

II. Composition of Protector Coated Tablets

| | |
|---|---|
| Tablets from 1 | 3.0 kg |
| Eudragit E | 0.3 kg |
| Kaolin | 0.10 kg |
| Talc | 0.05 kg |
| Acetone | 0.234 kg |
| Isopropyl alcohol | 0.281 kg |
| Ethylcellulose 2% | 1.500 kg |

Apply a 2% solution of ethylcellulose to the tablets for I in a perforated coating pan. Finely disperse kaolin and Talc in the Eudragit E solvent mixture using a propeller mixer. Apply this solution unto the ethylcellulose coated tablets in a perforated coating pan.

III. Composition of Enteric Coated Tablets

| | |
|---|---|
| Protector coated tablets from II | 3.450 kg |
| Hydroxypropyl methylcellulose acctate succinate | 0.345 kg |

Polymer Solution

| | |
|---|---|
| Hydroxypropyl methylcellulose acetate succinate | 0.345 kg |
| Triethyl citrate | 0.041 kg |
| Ethanol/water (80:20) | 0.807 kg |
| Pigment suspension | |
| Opadry | 0.034 kg |
| Talc | 0.034 kg |
| PEG 6000 | 0.015 kg |
| Water | 0.053 kg |
| | 1.329 kg |

Add the homogenized pigment and talc suspension to the polymer solution to form the enteric coating solution. Apply the enteric coating solution unto the protector coated tablets in perforated coating pan and dry in a tray dryer if necessary. One or more of the enteric coated tablets are filled into hard gelatin capsules.

Temperature and relative humidity of the manufacturing area should be no greater than 35° C. and 50%.

EXAMPLE 4

| | |
|---|---|
| Omeprazole | 20 mg |
| Lactose | 90 mg |
| Microcrystalline cellulose | 30 mg |
| Calcium sulfate | 30 mg |
| Sodium lauryl sulphate | 20 mg |
| PVP XL 10 | 4 mg |
| Talc | 15 mg |

Lactose, microcrystalline cellulose, calcium sulfate, sodium lauryl sulfate and omeprazole were blended in a planetary mixer. The blend was granulated with alcoholic solution and dried in t tray dryer of an LOD of <12%. The dried granules are milled and then blended with talc and PVP XL IO and pressed into pellets/tablets.

II. Composition of Protector Coated Pellets/Tablets

| | |
|---|---|
| Pellets/tablets from I | 3.00 kg |
| Polyethylene oxide (Polyox WSR N-750) | 0.060 kg |
| Kaolin | 0.010 kg |
| Talc | 0.010 kg |

Finely disperse polyethylene oxide, kaolin and talc in the solvent mixture using a propeller mixer. Apply the protector coat solution unto the pellets/tablets in a perforated coating pan.

III. Composition of Enteric Coated Pellets/Tablets

| | |
|---|---|
| Protector coated tablets from II | 3.000 kg |
| Hydroxypropyl methylcellulose acetate succina | 0.50 kg |
| Talc | 0.045 kg |
| Trienthyl citrate | 0.042 |
| Sodium lauryl sulphate | 0.005 |

Apply the enteric coating solution unto the protector coated pellets/tablets in a perforated coating pan and dry in a tray dryer if necessary. One or more of the enteric coated pellets/tablets are filled into hard gelatin capsules.

Temperature and relative humidity of the manufacturing area should be no greater than 35° C. and 50%.

EXAMPLE 5

I. Composition of Pellets/Tablets

| | |
|---|---|
| Omeprazole | 20 mg |
| Lactose | 75 mg |
| Microcrystalline cellulose | 40 mg |
| Calcium sulphate | 30 mg |
| Sodium layryl sulphate | 20 mg |
| Talc | 15 mg |

Lactose, microcrystalline cellulose, calcium sulfate, sodium layryl sulfate and omeprazole were blended in a planetary mixer. The homogeneous blend was blended with talc and in a V-blender and pressed into pellet/tablets.

II. Composition of Protector Coated Pellets/Tablets

| | |
|---|---|
| Pellet/tablets from I | 3.00 kg |
| Polyethylene oxide (Polyox WSR N-750) | 0.120 kg |
| Kaolin | 0.010 kg |
| Talc | 0.010 kg |

Finely disperse polyethylene oxide, kaolin and Talc in the solvent mixture using a propeller mixer. Apply the protector coat solution unto the pellets/tablets in a perforated coating pan.

III. Composition of Enteric Coated Pellets/Tablets

| | |
|---|---|
| Protector coated pellets/tablets from II | 3.450 kg |
| Hydroxypropyl methylcellulose acetate succinate** | 0.345 kg |

**from the following coating solution shown below for 3 kg batch

Polymer Solution

| | |
|---|---|
| Hydroxypropyl methylcellulose acetate succinate | 0.345 kg |
| Triethyl citrate | 0.041 kg |
| Ethanol/water (80:20) | 0.807 kg |
| Pigment suspension | |
| Opadry | 0.034 kg |
| Talc | 0.034 kg |
| PEG 6000 | 0.015 kg |
| Water | 0.053 kg |
| | 1.329 kg |

Add the homogenized pigment and talc suspension to the polymer solution to form the enteric coating solution. Apply the enteric coating solution unto the protector coated tablets in perforated coating pan and dry in a tray dryer if necessary, One or more of the enteric coated pellets/tablets are filled into hard gelatin capsules.

Temperature and relative humidity of the manufacturing area should be no greater than 35° C. and 50%.

EXAMPLE 6

I. Composition of Pellets/Tablets

| | |
|---|---|
| Omeprazole | 20 mg |
| Lactose | 100 mg |
| Calcium sulfate | 30 mg |
| Sodium lauryl sulphate | 20 mg |
| Microcrystalline cellulose | 15 mg |
| Sodium starch glycolate | 10 mg |
| Talc | 5 mg |

Lactose, microcrystalline cellulose, omeprazole, sodium lauryl sulfate, calcium sulfate and corn starch were blended in a planetary mixer. The blend was granulated with alcoholic solution and dried in a tray dryer to an LOD of 1%. The dried granules are blended with talc and sodium starch glycolate and pressed into pellets/tablets.

II. Composition of Protector Coated Pellets/Tablets

| | |
|---|---|
| Pellets/tables from I | 3.00 kg |
| Polyethylene oxide (Polyox WSR N-1O) | 0.120 kg |
| Kaolin | 0.010 kg |
| Talc | 0.010 kg |

Finely disperse polyethylene oxide, kaolin and Talc in the solvent mixture using a propeller mixer. Apply the protector coat solution unto the pellets/tablets in a perforated coating pan.

III. Composition of Enteric Coated Pellets/Tablets

| | |
|---|---|
| Protector coated pellets/tablets from II | 3.450 kg |
| Hydroxypropyl methlylcellulose acctate succinate** | 0.345 kg |

**from the following coating solution shown below for 3 kg batch

Polymer Solution

| | |
|---|---|
| Hydroxypropyl methycellulose acetate succinate | 0.345 kg |
| Triethyl citrate | 0.041 kg |
| Ethanol/water (80:20) | 0.807 kg |
| Pigment suspension | |
| Opadry | 0.034 kg |
| Talc | 0.034 kg |
| PEG 6000 | 0.015 kg |
| Water | 0.053 kg |

Add the homogenized pigment and talc suspension to the polymer solution to form the enteric coating solution. Apply the enteric coating solution unto the protector coated pellets/tablets in perforated coating pan and dry in a tray dryer if necessary. One or more of the enteric coated tablets are filled into hard gelatin capsules.

Temperature and relative humidity of the manufacturing area should be no greater than 35° C. and 50%.

What we claim:

1. A method for producing a pharmaceutical composition comprising an acid labile compound, said method comprising:
    combining doubt 1–75% by weight proton pump inhibitor compound and up to about 5% by weight disintegrant to form a core;
    coating said core with at least one protector coat layer used to separate and protect the proton pump inhibitor compound from acid reacting groups and gastric juice, said protector coat layer comprising from about 0.1% to about 10% aminoalkyl methacrylate copolymers; and
    providing at least one enteric coat layer which surrounds the protector coat layer and ensures delivery of over about 80% of the proton pump inhibitor compound to the small intestine.

2. The method of claim 1, wherein not less than about 0.1% acid sequestering compound is additionally combined with said proton pump inhibitor compound in said core.

3. The method of claim 2, wherein said acid sequestering compound is selected from the group consisting of aminoalkyl methacrylate copolymer and ethylcellulose.

4. The method of claim 3, wherein said acid sequestering compound is further admixed with inert pharmaceutical fillers selected from the group consisting of lactose, starch and microcrystalline cellulose.

5. The method of claim 1, wherein said protective coat layer additionally comprises an inert pharmaceutical filler selected from the group consisting of lactose, starch and microcrystalline cellulose.

6. The method of claim 5, wherein said protective coat layer additionally comprises a pharmaceutical excipient selected from the group consisting of plasticizers, pigment and anti-tacking agents.

7. The method of claim 6, wherein said disintegrant is selected from the group consisting of sodium starch glycolate, crospovidone, pregelatinized starch, methacrylic acid DVP, croscarmellose sodium and cross-lined carboxymethyl cellulose.

8. The method of claim 7, wherein said disintegrant is additionally mixed with an inert pharmaceutical filler selected form the group consisting of lactose, calcium sulfate and microcrystalline cellulose.

9. The method of claim 1, wherein said enteric coat layer is present in an amount of about 0.1% to 50% by weight.

10. The method of claim 9, wherein said proton pump inhibitor compound is selected from the group consisting of omeprazole, 5-methoxy-2-(4-methoxy-3,5dimethyl-2-pyridinyl methyl sulfinyl-1H-benzimidazole, lansoprazole, 2-(2-diriiethylaminobenzyl)sulfinyl-benzimidazole, pantoprazole and their related ammonium, sodium, magnesium and calcium salts.

11. The method of claim 10, wherein said core is provided as a tablet or pellet.

12. The method of claim 10, wherein said core is provided in a gelatin capsule.

13. The method of claim 10, wherein said enteric coating is selected from the group consisting of shellac, constituent aliphatic polyhydroxy acids of shellac, acetic and mono succinic acid esters of hydroxyproply methylcellulose, and methacrylic acid copolymers.

14. The method of claim 13, wherein said enteric coating additionally comprises a pharmaceutical excipient selected from the group consisting of plasticizers, pigments and colorants.

15. The method of claim 1, wherein said protective coating comprises carrageenan or nonionic polyethylene oxide polymers having a molecular weight of over 20,000 daltons.

\* \* \* \* \*

UNITED STATES PATENT AND TRADEMARK OFFICE
CERTIFICATE OF CORRECTION

PATENT NO. : 6,479,075 B1
DATED : November 12, 2002
INVENTOR(S) : Odidi et al.

It is certified that error appears in the above-identified patent and that said Letters Patent is hereby corrected as shown below:

Column 10,
Line 47, "doubt" should read -- about --.

Signed and Sealed this

Fourteenth Day of December, 2004

JON W. DUDAS
*Director of the United States Patent and Trademark Office*